United States Patent
Boublik et al.

(10) Patent No.: US 6,207,163 B1
(45) Date of Patent: Mar. 27, 2001

(54) HYDRATION COMPOSITIONS FOR HUMAN OR ANIMAL BODIES

(75) Inventors: Jaroslav H. Boublik, Elwood; Leonie Jennifer Hibbert, Kew; Diana Joy Killen, Eastkew; Grofrey Melvillo Spalding, Kew, all of (AU)

(73) Assignee: Aquaconnexions Pty Ltd., Victoria (AU)

( * ) Notice: Subject to any disclaimer, the term of this patent is extended or adjusted under 35 U.S.C. 154(b) by 0 days.

(21) Appl. No.: 08/809,805

(22) PCT Filed: Oct. 6, 1995

(86) PCT No.: PCT/AU95/00663

§ 371 Date: Feb. 25, 1998

§ 102(e) Date: Feb. 25, 1998

(87) PCT Pub. No.: WO96/11015

PCT Pub. Date: Apr. 18, 1996

(Under 37 CFR 1.47)

(30) Foreign Application Priority Data

Oct. 7, 1994 (AU) .................................................. PM8667

(51) Int. Cl.⁷ .................................................... A01N 65/00
(52) U.S. Cl. .......................................................... 424/195.1
(58) Field of Search ........................................... 424/195.1

(56) References Cited

FOREIGN PATENT DOCUMENTS

| 47176 | * | 11/1979 | (AU) . |
| 58377 | * | 11/1980 | (AU) . |
| 61233 | * | 12/1986 | (AU) . |
| 2623397 | * | 5/1989 | (FR) . |

* cited by examiner

Primary Examiner—Herbert J. Lilling
(74) Attorney, Agent, or Firm—Woodcock Washburn Kurtz Mackiewicz & Norris LLP

(57) ABSTRACT

A hydration composition for the body is provided which essentially includes the synergistic combination of: (a) *Hydrastis canadensis* (common name: Golden Seal), b) *Ulmus fulva* (common name: Slippery Elm), and (c) *Smilax ornata* (common name: Salsaparilla). The above hydration composition may be prepared in homoeopathic or non-homocopathic form. The homoeopathic hydration composition may be prepared by any one of the following methods comprising: (i) forming separate homoeopathic preparations from components (a, b and c) mentioned hereinabove, and subsequently mixing said homoeopathic preparations; (ii) mixing extracts of components (a, b and c) and forming the resultant mixture into a homoepathic composition; and (iii) preparing a first homoeopathic composition as in (i) and (ii) above (with optional additional ingredients), and further diluting said first composition to form a second homoeopathic composition.

18 Claims, No Drawings

HYDRATION COMPOSITIONS FOR HUMAN OR ANIMAL BODIES

This application is a 371 of PCT/AU95/00663 filed on Oct. 1995.

FIELD OF THE INVENTION

This invention relates to hydration compositions for human or animal bodies (hereinafter referred to as "body or bodies"). "Hydration" in this context may be defined as a state of optimal water management in the body.

BACKGROUND OF THE INVENTION

It is well accepted and established that water is the most abundant nutrient found in the body, accounting for roughly two-thirds of the adult body weight. It is also the most important nutrient and is the primary transporter of other nutrients throughout the body. It is necessary for all building functions and all body processes including digestion, absorption, circulation, brain function and excretion.

Energy and vitality depend on how well the body breaks down, assimilates and converts food to energy. Simply eating well or taking nutritional supplements will make little difference if the body is not able to digest and fully absorb all the nutrients consumed.

It has accordingly been recognised that all processes in the body depend on water. However, this does not mean just water intake, but rather water utilization or absorption at the cellular level.

Should the body's hydration become compromised, fatigue may be one of the first a lost obvious signs. Others include depression, poor digestion, joint problems, aging skin and general skin problems, candida difficulties, constipation, difficulty concentrating and an aversion to drinking water or unsatisfied thirst.

OBJECTIVES OF THE INVENTION

It is the primary objective of the present invention to provide hydration compositions to enhance hydration in the body.

It is a further objective of the invention to provide compositions which enhance oxygen uptake at a cellular level.

SUMMARY OF THE INVENTION

Accordingly, the invention provides a hydration composition for the body essentially including the synergistic combination of:
(a) Hydrastis canadensis (common name—Golden Seal)
(b) Ulmus fulva (common name—Slippery Elm), and
(c) Smilax ornata (common name—Sarsaparilla).

Preferably, the above composition is prepared in homoeopathic form.

The above composition may be prepared by any one of the following methods comprising:
(i) forming separate homoeopathic preparations from components (a), (b) and (c) mentioned hereinabove, and subsequently mixing said homoeopathic preparations;
(ii) mixing extracts of components (a), (b) and (c) and forming the resultant mixture into a homoeopathic composition; and
(iii) preparing a first homoeopathic composition as in (i) and (ii) above (with optional ingredients mentioned hereinbelow), and further diluting said first composition to form a second homoeopathic composition.

PREFERRED FEATURES OF THE INVENTION

Advantageously, the hydration compositions may comprise one or more additional ingredients selected from homoeopathic and non-homoeopathic preparations, e.g., vanilla, "nervacomp", chlorophyll, echinacea augustifolia, opuntia vulgaris, micellized alpha-tocopherol, and iodine. The term "nervacomp" is a homoeopathic mixture comprising:

Ignatia 8c
Hyoscyamus nig 8c
Oenanthe crocata 8c
Passiflora 8c
Stramonium 8c
Zincum met 8c The compositions may also advantageously contain essential oils, e.g., French organic lavender and frankincense; Australian bush flower essences, e.g., Peach Flowered Tea Tree, Sturt Desert Rose, Slender Rice Flow, Alpine Mint Bush, Tall Yellow Top, Green Spider Orchid, Red Helmet Orchid and Wedding Bush; Bach Flower Essences, e.g., Oak, Larch, Chinese Plumbago, Aspen, Clematis, Water Violet, Beech, Rock Water; and amino acids, e.g. histidine, glutamine, arginine, glycine, lysine, leucine, isoleucine, valine, methionine and aspartic acid.

The compositions are preferably formulated so as to be (i) gender specific and (ii) time-of-day specific (i.e. upon-rising, upon-retiring) to account for (i) the known differences in water metabolism in men and women in response to sex hormones and (ii) optimisation of the support of water management in the sleeping and waking cycles of metabolism. The upon-retiring compositions support the transport of oxygen into cells further improving the clearance of metabolic waste products and enhancing cellular energy production.

Advantageously components (a) to (c) mentioned hereinabove are present or are used in the homoeopathic compositions, in approximately equal proportions by volume.

EXAMPLES ILLUSTRATING THE INVENTION

The invention will now be described with reference to the following non-limiting examples.

Example 1

Hydration compositions for females, upon-rising (20 ml)

| | |
|---|---|
| Hydrastis canadensis 30c | 4.5 ml |
| Ulmus fulva 30c | 4.0 |
| Smilax ornata 30c | 4.5 |
| Vanilla tincture 1:2 | 4.5 |
| nervacomp | .75 |
| Filtered spring water | 1.75 |
| *Peach Flowered Tea Tree | 1 drop |
| *Sturt Desert Rose | 1 drop |

The above composition was prepared as follows:

The indicated volumes of all ingredients with the exception of the flower essences are combined and mixed. The appropriate number of drops of the flower essences are added to this mixture.

Alternatively the ingredients are combined in appropriate proportions to a final volume of, for example, 1 liter and mixed. Flower essences are added to this mixture. In this case, the volume of the flower essences are 1.5 ml Peach Flowered Tea Tree and 1.5 ml Sturt Desert Rose.

Example 2

Hydration compositions for female, upon-retiring (20 ml)

| | |
|---|---|
| *Smilax ornata* 11x | 5.5 ml |
| *Ulmus fulva* 11x | 5.0 |
| *Hydrastis canadensis* 11x | 5.0 |
| Chlorophyll 1:5 | 1.7 |
| *Echinacea augustifolia* 1:1 | 1.0 |
| Filtered spring water | 1.8 |
| *Slender Rice Flower | 1 drop |
| *Alpine Mint Bush | 1 drop |

The composition was prepared as in Example 1 except that the volumes for flower essences for 1 liter are 1.5 ml Slender Rice Flower and 1.5 ml Mint Bush.

Example 3

Hydration composition for males, upon-rising (20 ml)

| | |
|---|---|
| *Hydrastis canadensis* 30c | 3.5 ml |
| *Ulmus fulva* 30c | 3.5 |
| *Smilax ornata* 30c | 3.5 |
| Vanilla tincture 1:2 | 6.0 |
| *Opuntia vulgaris* 12x | 3.5 |
| *Tall Yellow Top | 2 drops |
| *Green Spider Orchid | 1 drop |

The composition was prepared as in Example 1 except that the volumes for flower essences for 1 liter are 2 ml Tall Yellow Top and 1.5 ml Green Spider Orchid.

Example 4

Hydration composition for males, upon-retiring (20 ml)

| | |
|---|---|
| *Hydrastis canadensis* 30c | 4.0 ml |
| *Smilax ornata* 30c | 4.0 |
| *Ulmus fulva* 30c | 4.0 |
| Micellized α-tocopherol 10c | 4.0 |
| Iodine 12x | 4.0 |
| French Organic Lavender | 7 drops/liter |
| *Red Helmet Orchid | 1 drop |
| *Wedding Bush | 1 drop |
| Micellized α-tocopherol | 3 drops |

The composition was prepared as in Example 1 except that for 20 ml bottles, micellized α-tocopherol is added singly with the flower essences. For 1 liter, volumes of flower essences are 1.5 ml Red Helmet and 1.5 ml Wedding Bush, and micellized α-tocopherol—3 mls.

Example 5

Hydration compositions for females, upon rising (20 ml)

| | |
|---|---|
| *Hydrastis canadensis* 30c | 4.5 ml |
| *Ulmus fulva* 30c | 4.0 |
| *Smilax ornata* 30c | 4.5 |

-continued

| | |
|---|---|
| Vanilla tincture | 4.5 |
| Nervacomp | 0.75 |
| Filtered spring water | 1.75 |
| *Oak | 1 drop |
| *Larch | 1 drop |
| *Chinese plumbago | 1 drop |

The composition was prepared as in Example 1 except that the volumes for flower essences for 1 liter are 1 ml Oak, 1 ml Larch and 1 ml Chinese plumbago.

Example 6

Hydration compositions for males, upon rising (20 ml)

| | |
|---|---|
| *Hydrastis canadensis* 30c | 3.5 ml |
| *Ulmus fulva* 30c | 3.5 |
| *Smilax ornata* 30c | 3.5 |
| Vanilla tincture 1:2 | 6.0 |
| *Opuntia Vulgaris* 12x | 3.5 |
| *Oak | 1 drop |
| *Aspen | 1 drop |

The composition was prepared as in Example 1 except that the volumes for flower essences for 1 liter are 1.5 ml Oak and 1.5 ml Aspen.

Example 7

Hydration compositions for females, upon retiring (20 ml)

| | |
|---|---|
| *Hydrastis canadensis* 11x | 5.5 ml |
| *Ulmus fulva* 11x | 5.0 |
| *Smilax ornata* 11x | 5.0 |
| Chlorophyll 1:5 | 1.7 |
| *Echinacea augustifolia* 1:1 | 1.0 |
| Filtered spring water | 1.8 |
| *Clematis | 1 drop |
| *Water Violet | 1 drop |

The composition was prepared as in Example 1 except that the volumes for flower essences for 1 liter are 1.5 ml Clematis and 1.5 ml Water Violet.

Example 8

Hydration compositions for males, upon retiring (20 ml)

| | |
|---|---|
| *Hydrastis canadensis* 30c | 4.0 ml |
| *Ulmus fulva* 30c | 4.0 |
| *Smilax ornata* 30c | 4.0 |
| Micellized α-tocopherol 10c | 4.0 |
| Iodine 12x | 4.0 |
| French Organic Lavender oil | 7 drops/liter |
| *Beech | 1 drop |
| *Rock Water | 1 drop |

The composition was prepared as in Example 1 except that for 20 ml bottles micellized α-tocopherol is added singly with the flower essences. For 1 liter the volumes for flower essences are 1.5 ml Clematis and 1.5 ml Water Violet and micellized α-tocopherol 3 mls.

Flower essences to be added individually to each 20 ml bottle 1 drop=0.0625 ml. This may be changed where the volume is one liter.

The homoeopathic preparations referred to above are prepared as follows:

The herbal source material is ground or macerated and infused with alcohol (ethanol) to obtain a first extract called the mother tincture. The homoeopathic is prepared by successive dilutions of this mother tincture. For the x series the dilutions are 1 in 10; for the c series the dilutions are 1 in 100. Thus an 11x preparation is eleven 1 in 10 dilutions of the mother tincture. For a 30c preparation, thirty 1 in 100 dilutions of the mother tincture are required. The dilutions are made in alcohol with each new mixture being vigorously shaken and then impacted on a hard surface—a process known as succussion.

RESULTS OBTAINED BY THE INVENTION

The hydration compositions of the present invention are considered to enhance and facilitate the passage of water and water-borne nutrients at the level of initial absorption through the small intestine and subsequently at the level of cellular absorption. The mechanisms by which this occurs is yet to be specifically identified but is likely to include opening water-transport pores in the cell membrane. The gender specificity of the preferred compositions correlates with the known differences in water metabolism in men and women in response to sex hormones. The time-of-day specificity of the preferred compositions have been designed to optimise the support of water management in the sleeping and waking cycles of metabolism. In addition the upon-retiring compositions support the transport of oxygen into cells further improving the clearance of metabolic waste products and enhancing cellular energy production.

It is impossible to break down the action of each of the components of the compositions in the conventional way it is done in pharmacology because it is believed that the components interact and operate synergistically. Thus the removal of one component may dramatically alter the efficacy of the compositions.

The compositions are not comparable with existing "hydration drinks" such as Gatorade™ or Sports Plush™ in that they do not provide hydrating liquid, nutrients or electrolytes. They cannot be compared to pharmacologically active substances such as diuretics or membrane; permeabilisers which operate at specific sites (i.e. kidney and gut) and in general only affect the traffic of water in one direction. Rather they must be compared with any product which seeks to optimise the management of water via increased uptake, increased clearance and better distribution at a general cellular level.

The claims defining the invention are as follows:

1. A hydration composition for the body comprising a synergistic combination of alcohol extracts of:
   (a) Hydrastis canadensis,
   (b) Ulmus fulva, and
   (c) Smilax ornata wherein said composition is in a homeopathic or non-homeopathic form.

2. A hydration composition of claim 1, wherein said composition is in a homoeopathic form.

3. The composition of claim 1 or claim 2, further comprising homoeopathic and non-homoeopathic preparations selected from the group consisting of alcohol extracts of vanilla, nervacomp, chlorophyll, echinacea augustifolia, opuntia vulgaris, micellized α-tocopherol, and iodine.

4. The composition of claim 3 further comprising at least one material selected from the group consisting of:

(1) essential oils comprising alcohol extracts of French Organic Lavender or Frankincese;

(2) Australian bush flower essences comprising alcohol extracts of Peach Flowered Tea Tree, Sturt Desert Rose, Slender Rice Flower, Alpine Mint Bush, Tall Yellow Top, Green Spider Orchid, Red Helmet Orchid or Wedding Bush;

(3) Bach Flower Essences comprising alcohol extracts of Oak Larch, Chinese Plubago, Aspen, Clematis, Water Violet, Beech or Rock Water; and (4) Amino acids selected from the group consisting of histidine, glutamine, arginine, glycine, lysine, leucine, isoleucine, valine, methionine and aspartic acid.

5. A hydration composition for a female body comprising:

| | |
|---|---|
| Hydrastis canadensis | 4.5 ml |
| Ulmus fulva | 4.0 ml |
| Smilax ornata | 4.5 ml |
| Vanilla tincture | 4.5 ml |
| Nervacomp | 0.75 ml |
| Filtered spring water | 1.75 ml |
| Peach Flowered Tea Tree | 0.0625 ml |
| Sturt Desert Rose | 0.0625 ml | wherein the Hydrastis canadensis, Ulmus fulva and Smilax ornata are produced from thirty 1:100 dilutions of initial alcohol extracts of the herbal materials, the vanilla tincture is produced from a 1:2 dilution of an initial alcohol extract and the Nervacomp Peach Flowered Tea Tree and Sturt Desert Rose are present in the composition as alcohol extracts.

6. A hydration composition for a female body comprising:

| | |
|---|---|
| Smilax ornata | 5.5 ml |
| Ulmus Fulva | 5.0 ml |
| Hydrastis canadensis | 5.0 ml |
| Chlorophyll | 1.7 ml |
| Echinacea augustifolia | 1.0 ml |
| Filtered spring water | 1.8 ml |
| Slender Rice Flower | 0.0625 ml |
| Alpine Mint Bush | 0.0625 ml | wherein the Smilax ornata, Ulmus fulva and Hydrastis canadensis are produced from eleven 1:10 dilutions of initial alcohol extracts of the herbal materials, the chlorophyll is produced from a 1:5 dilution of an initial alcohol extract, the Echinacea augustifolia is produced from a 1:1 dilution of an initial alcohol extract of the herbal material, and the Slender Rice Flower and Alpine Mint Bush are present in the composition as alcohol extracts.

7. A hydration composition for a male body comprising:

| | |
|---|---|
| Hydrastis canadensis | 3.5 ml |
| Ulmus fulva | 3.5 ml |
| Smilax ornata | 3.5 ml |
| Vanilla tincture | 6.0 ml |
| Opuntia vulgaris | 3.5 ml |
| Tall Yellow Top | 0.125 ml |
| Green Spider Orchid | 0.0625 ml | wherein the Hydrastis canadensis, Ulmus fulva and Smilax ornata are produced from thirty 1:100 dilutions of initial alcohol extracts of herbal materials, the vanilla tincture is produced from a 1:2 dilution of an initial alcohol extract, the Opuntia vulgaris is produced from twelve 1:10 dilutions of an initial alcohol extract of the herbal material, and the Tall Yellow Top and Green Spider Orchid are present in the composition as alcohol extracts.

8. A hydration composition for a male body comprising:

|  |  |
|---|---|
| Hydrastis canadensis | 4.0 ml |
| Smilax ornata | 4.0 ml |
| Ulmus fulva | 4.0 ml |
| Micellized α-tocopherol | 4.0 ml |
| Iodine | 4.0 ml |
| French Organic Lavender | 0.4375 ml |
| Red Helmet Orchid | 0.0625 ml |
| Wedding Bush | 0.0625 ml | wherein the Hydrastis canadensis, Smilax ornata and Ulmus fulva are produced from thirty 1:100 dilutions of initial alcohol extracts of herbal materials, the micellized a-tocopherol is produced from ten 1:100 dilutions of an initial alcohol extract, the iodine is produced from twelve 1:10 dilutions of an initial alcohol extract, and the French Organic Lavender. Red Helmet Orchid and Wedding Bush are present in the composition as alcohol extracts.

9. A hydration composition for a female body comprising:

|  |  |
|---|---|
| Hydrastis canadensis | 4.5 ml |
| Ulmus fulva | 4.0 ml |
| Smilax ornata | 4.5 ml |
| Vanilla tincture | 4.5 ml |
| Nervacomp | 0.75 ml |
| Filtered spring water | 1.75 ml |
| Oak | 0.0625 ml |
| Larch | 0.0625 ml |
| Chinese plumbago | 0.0625 ml | wherein the Hydrastis canadensis, Ulmus fulva and Smilax ornata are produced from thirty 1:100 dilutions of initial alcohol extracts of the herbal materials, and the vanilla tincture, Nervacomp. Oak. Larch and Chinese plumbago are present in the composition as alcohol extracts.

10. A hydration composition for a male body comprising:

|  |  |
|---|---|
| Hydrastis canadensis | 3.5 ml |
| Ulmus fulva | 3.5 ml |
| Smilax ornata | 3.5 ml |
| Vanilla tincture | 6.0 ml |
| Opuntia vulgaris | 3.5 ml |
| Oak | 0.0625 ml |
| Aspen | 0.0625 ml | wherein the Hydrastis canadensis, Ulmus fulva and Smilax ornata are produced from thirty 1I:100 dilutions of initial alcohol extracts of the herbal materials, the Opuntia vulgaris is produced from twelve 1:10 dilutions of an initial alcohol extract of the herbal material, the vanilla tincture is produced from a 1:2 dilution of an initial alcohol extract, and the Oak and Aspen are present in the composition as alcohol extracts.

11. A hydration composition for a female body comprising:

|  |  |
|---|---|
| Hydrastis canadensis | 5.5 ml |
| Ulmus Fulva | 5.0 ml |

-continued

|  |  |
|---|---|
| Smilax ornata | 5.0 ml |
| Chlorophyll | 1.7 ml |
| Echinacea augustifolia | 1.0 ml |
| Filtered spring water | 1.8 ml |
| Clematis | 0.0625 ml |
| Water Violet | 0.0625 ml | wherein the Hydrastis canadensis, Ulmus fulva and Smilax ornata are produced from eleven 1:10 dilutions of initial alcohol extracts of the herbal materials, the chlorophyll is produced from a 1:5 dilution of an initial alcohol extract, the Echinacea augustifolia is produced from a 1:1 dilution of an initial alcohol extract of the herbal material, and the Clematis and Water Violet are present in the composition as alcohol extracts.

12. A hydration composition for a male body comprising:

|  |  |
|---|---|
| Hydrastis canadensis | 4.0 ml |
| Ulmus fulva | 4.0 ml |
| Smilax ornata | 4.0 ml |
| Micellized α-tocopherol | 4.0 ml |
| Iodine | 4.0 ml |
| French Organic Lavender oil | 0.4375 ml |
| Beech | 0.0625 ml |
| Rock water | 0.0625 ml | wherein the Hydrastis canadensis, Ulmus falva and Smilax ornata are produced from thirty 1:100 dilutions of initial alcohol extracts of the herbal materials, the micellized α-tocopherol is produced from ten 1:100 dilutions of an initial alcohol extract, the iodine is produced from twelve 1:10 dilutions of an initial alcohol extract, and the French Organic Lavender and Beech are present in the composition as alcohol extracts.

13. A hydration composition as in claim 2, wherein components (a) to (c) are present in the homoeopathic compositions in equal proportions by volume.

14. A method of preparing a hydration composition which comprises alcohol extracts of:
(a) Hydrastis canadensis,
(b) Ulmus fulva, and
(c) Smilax ornata, comprising the steps of:
forming separate homeopathic preparations from alcohol extracts of components (a), (b) and (c) and subsequently
mixing said homeopathic preparations, thereby producing said hydration composition.

15. A method of preparing a hydration composition which comprises alcohol extracts of:
(a) Hydrastis canadensis,
(b) Ulmus fulva, and
(c) Smilax ornata, comprising the steps of:
mixing alcohol extracts of components (a), (b) and (c) and forming the resultant mixture into a homeopathic composition, thereby producing said hydration composition.

16. A method of claim 14 or 15 further comprising diluting said hydration composition to form a second homoeopathic hydration composition.

17. A method of claim 16, further comprising adding a homoeopathic or non-homoeopathic preparation selected from the group consisting of alcohol extracts of vanilla, nervacomp, chlorophyll, echinacea augustifolia, opuntia vulgaris, micellized α-tocopherol, and iodine to said hydration composition.

18. A method of claim 16, further comprising adding at least one material selected from the group consisting of:
  (1) essential oils comprising alcohol extracts of French Organic Lavender or Frankincese;
  (2) Australian bush flower essences comprising alcohol extracts of Peach Flowered Tea Tree, Sturt Desert Rose, Slender Rice Flower, Alpine Mint Bush, Tall Yellow Top, Green Spider Orchid, Red Helmet Orchid or Wedding Bush;
  (3) Bach Flower Essences comprising alcohol extracts of Oak Larch, Chinese Plubago, Aspen, Clematis, Water Violet, Beech or Rock Water; and
  (4) Amino acids selected from the group consisting of histidine, glutamine, arginine, glycine, lysine, leucine, isoleucine, valine, methionine and aspartic acid, to said hydration composition.

* * * * *